(12) United States Patent
Kinoshita et al.

(10) Patent No.: US 6,329,189 B1
(45) Date of Patent: Dec. 11, 2001

(54) ENZYME PRODUCING TARTARIC ACID ETHER COMPOUND AND PROCESS FOR PRODUCING TARTARIC ACID ETHER COMPOUNDS USING THIS ENZYME

(75) Inventors: Emiko Kinoshita; Tetsuo Aishima; Yoshinori Ozawa, all of Noda (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/293,986

(22) Filed: Apr. 19, 1999

(30) Foreign Application Priority Data

Apr. 28, 1998 (JP) .................................................. 10-117672

(51) Int. Cl.[7] .............................. C12N 9/88; C12P 17/06
(52) U.S. Cl. ............................................ 435/232; 435/125
(58) Field of Search ...................................... 435/232, 125

(56) References Cited

FOREIGN PATENT DOCUMENTS

| 9-110857 | 4/1997 | (JP) . |
| 10-059956 | 3/1998 | (JP) . |

Primary Examiner—Herbert J. Lilling
(74) Attorney, Agent, or Firm—Banner & Witcoff, Ltd.

(57) ABSTRACT

Disclosed in this invention are a novel enzyme producing tartaric acid ether compound which catalyzes a reaction of producing a tartaric acid ether compound in which the phenolic hydroxyl group(s) of a flavonoid or its analogous compound having at least one phenolic hydroxyl group is (are) acted to the epoxy ring of an epoxysuccinic acid to form ether linkage of one or more tartaric acid residues, a process for producing a tartaric acid ether compound by acting the enzyme in the presence of an epoxy-succinic acid and a flavonoid or its analogous compound having at least one phenolic hydroxyl group, and novel tartaric acid ether compounds in which the epoxy ring of an epoxysuccinic acid is bound to the phenolic hydroxyl group(s) of a flavonoid or its analogous compound to form ether linkage of one or more tartaric acid residues. These compounds are useful as a component material of pharmaceuticals and functional foods.

4 Claims, 3 Drawing Sheets

— ← 17.2K

ENZYME PRODUCING TARTARIC ACID ETHER COMPOUND AND PROCESS FOR PRODUCING TARTARIC ACID ETHER COMPOUNDS USING THIS ENZYME

BACKGROUND OF THE INVENTION

1. Field of the Invention

The present invention relates to the novel tartaric acid ether compounds useful as pharmaceuticals, functional foods and the like. More particularly, it relates to a novel enzyme producing tartaric acid ether compound which catalyzes a reaction of producing a tartaric acid ether compound in which the phenolic hydroxyl group(s) of flavonoids or the analogous compounds having phenolic hydroxyl group(s) is acted to an epoxy ring of an epoxysuccinic acid to form an ether linkage, an enzymatic process for producing the tartaric acid ether compounds using the said enzyme, and the novel tartaric acid ether compounds.

2. Description of the Related Prior Art

It is known that 2-hydroxy-3-[[3-(4-hydroxyphenyl)-4-oxo-4H-1-benzopyran-7-yl]oxy]-butanedioic acid (see "Isoflavone derivative peak A" in JP-A-9-110857), 2-hydroxy-3-[[5-hydroxy-3-(4-hydroxyphenyl)-4-oxo-4H-1-benzopyran-7-yl]oxy]-butanedioic acid (see "Isoflavone derivative peak B" in JP-A-9-110857) and 2-[[5,8-dihydroxy-3-(4-hydroxyphenyl)-4-oxo-4H-1-benzopyran-7-yl]oxy]-3-hydroxy-butanedioic acid (see "Isoflavone derivative peak A" in JP-A-10-59956), which are the tartaric acid ether compounds and the isoflavone derivatives, show a prominent inhibitory action against histidine decarboxylase (HDC) which takes part in the biosynthesis of histamine causative of ulcers and allergic diseases, and thus are very useful for the preparation of pharmaceuticals and functional foods free from harmful side effects.

Hitherto, despite their manifold physiological activities such as antioxidant action, HDC inhibitory action, estrogen-like action and anti-ulcer action, many of the flavonoids or their analogous compounds have fallen short of exhibiting their potential efficacy in the living body, just because of their low solubility in water.

The glycosides of flavonoids or their analogues show high solubility in water but are unstable in their structure. In contrast, the tartaric acid ether compounds of flavonoids or their analogues are very stable structurally.

In view of the above, it is significantly important to provide the tartaric acid ether compounds with high water solubility and stable structure, for example, the tartaric acid ether compounds of flavonoids and their analogues. Hitherto, various methods, such as synthesis through substitution reaction, synthesis through addition reaction, synthesis through leaving reaction or condensation reaction, synthesis through oxidation reaction and synthesis through reduction reaction, have been proposed and used for producing the ether compounds, but any of these methods has recourse to a chemical reaction and involves complicate operations and steps in connection with the reaction conditions and reaction reagents, and also requires specific synthesizing equipment. On the other hand, these has not entirely been known the technique for producing the tartaric acid ether compounds at low cost and with ease according to the enzyme process.

SUMMARY OF THE INVENTION

The present invention has been made with the object of overcoming these prior art problems in the synthesis of the tartaric acid ether compounds, finding out a novel enzyme capable of producing the tartaric acid ether compounds useful for the pharmahydroxy-butanedioic ceuticals and functional foods, and providing a process for producing the tartaric acid ether compounds with high water solubility and stable structure at low cost and with high precision and ease by using the said enzyme, while also offering the novel tartaric acid ether compounds.

In the course of the studies for attaining the above object, the present inventors found that the microorganisms belonging to the genus Aspergillus are capable of yielding a novel enzyme which is productive of the tartaric acid ether compounds by letting the phenolic hydroxyl group(s) of a flavonoid or its analogous compound having at least one phenolic hydroxyl group react with the epoxy ring of an epoxysuccinic acid, and that use of such an enzyme enables easy enzymatic formation of various tartaric acid ether compounds. The present invention has been completed on the basis of the above finding.

Thus, the present invention provides a novel enzyme producing tartaric acid ether compound which catalyzes a reaction of forming a tartaric acid ether compound in which the phenolic hydroxyl group(s) of a flavonoid or its analogous compound having at least one phenolic hydroxyl group is(are) acted to the epoxy ring of an epoxysuccinic acid to form ether linkage of one or more tartaric acid residues. The present invention also provides a process for producing the tartaric acid ether compounds, which comprises acting the said novel enzyme producing tartaric acid ether compound in the presence of an epoxysuccinic acid and a flavonoid or its analogous compound having at least one phenolic hydroxyl group. It is also envisaged in the present invention to provide the novel tartaric acid ether compounds in which the phenolic hydroxyl group(s) of a flavonoid or its analogous compound having at least one phenolic hydroxyl group is reacted with the epoxy ring of an epoxysuccinic acid to form ether linkage of one or more tartaric acid residues.

BRIEF DESCRIPTION OF THE DRAWINGS

Figure 3:
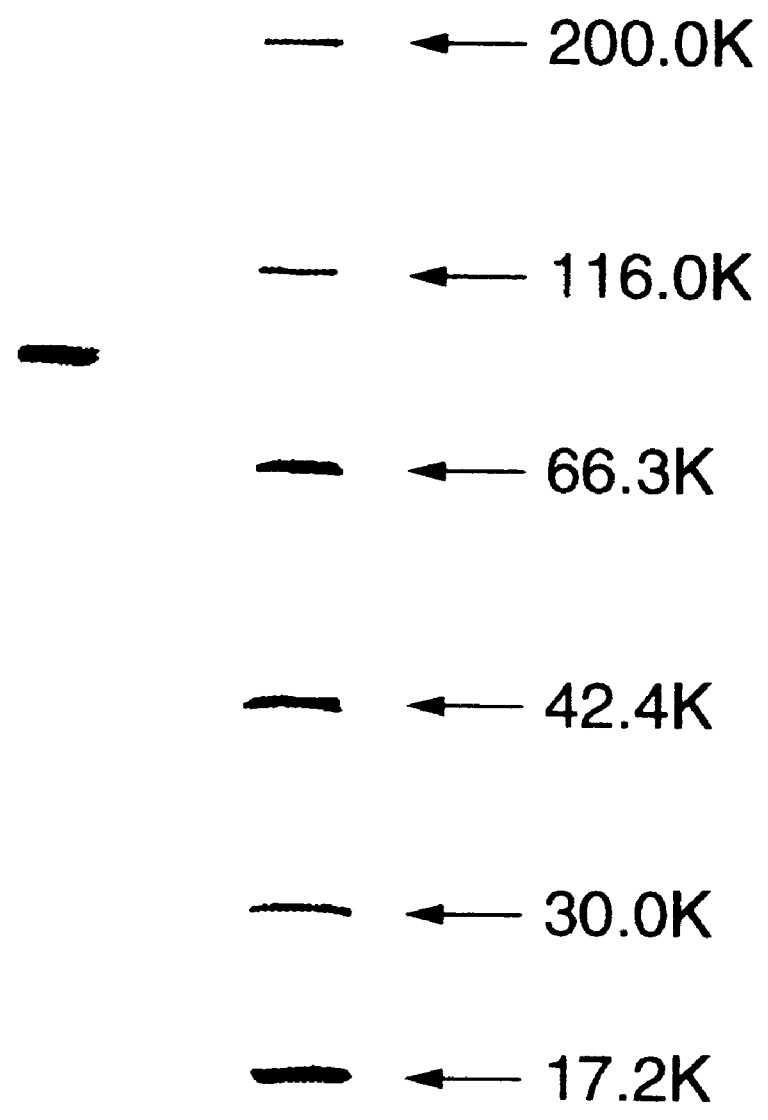

FIG. 3 is an electrophoretic diagram of an enzyme according to the present invention.

DETAILED DESCRIPTION OF THE INVENTION

Figure 1:
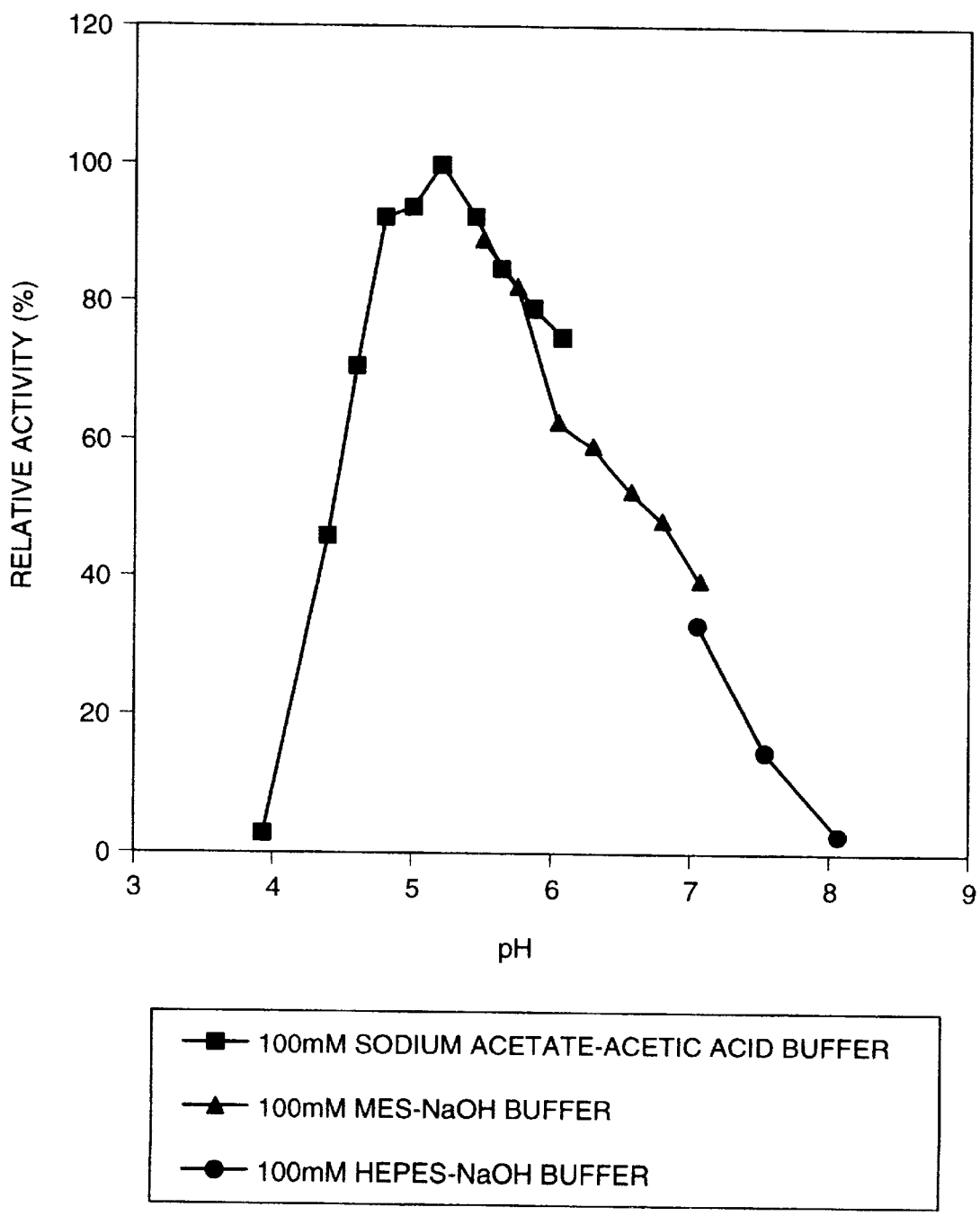
FIG. 1 is a graph showing the optimal pH range of an enzyme according to the present invention.

The present invention will be explained in further detail.

First, the physicochemical properties of the novel enzymes producing tartaric acid ether compound according to the present invention (hereinafter referred to as "the enzyme of the present invention" or simply as "the present enzyme") are described.

(1) Action:

The enzyme of the present invention catalyzes a tartaric acid ether compound forming reaction in which the phenolic hydroxyl group(s) of a flavonoid or its analogous compound having at least one phenolic hydroxyl group is(are) acted to the epoxy ring of an epoxysuccicic acid to form ether linkage of one or more tartaric acid residues.

"Epoxysuccinic acid" referred to in the present invention designates (±)-trans-epoxysuccinic acid, cis-epoxysuccinic acid and the like. "Flavonoids or their analoguous compounds having at least one phenolic hydroxyl group" used in the present invention may include any compounds having at least one phenolic hydroxyl group, which include, as examples of the flavonoids having at least one phenolic hydroxyl group, isoflavones, flavones, flavonols, flavanones, dihydroflavonols and aurones, and as examples of the flavonoid analogous compounds having at least one phenolic hydroxyl group, include coumarins, chalcones, coumaranones, chromones and rotenoids. More specifically, examples of isoflavones include daidzein, genistein, 4',6,7-trihydroxyisoflavone and biochanin A. Examples of flavones include apigenin and baicalein. Examples of flavonols include kaempferol and quercetin. Examples of flavanones include naringenin and hesperetin. Examples of dihydroflavonols include (+)-taxifolin and phellamurin. Examples of aurones include sulfuretin and leptosidin. Examples of coumarins include 5,7-dihydroxy-4-methylcoumarin and aesculetin. Examples of chalcones include 2',4',6',3,4-pentahydroxychalcone. Examples of coumaranones include 6-hydroxy-2H-benzofuran-3-one and 6-hydroxy-butylphthalide. Examples of chromones include eugenin and eugenitin. Examples of rotenoids include courmestrol and maackiain.

With an epoxysuccinic acid allowed to coexist with a flavonoid or its analogous compound having at least one phenolic hydroxyl group as mentioned above, the epoxy ring of said epoxysuccinic acid acts to the phenolic hydroxyl group(s) of said flavonoid or its analogous compound to produce a tartaric acid ether compound having ether linkage of one or more tartaric acid residues. Thus, it is possible to produce the different types of tartaric acid ether compound by acting the epoxysuccinic acid to the various types of flavonoid or flavonoid analogous compound having at least one phenolic hydroxyl group. For instance, in the presence of (±)-trans-epoxysuccinic acid and flavones having a phenolic hydroxyl group in combination, the present enzyme catalyzes the production reaction of a tartaric acid ether compound of the flavones.

(2) Substrate Specificity:

As is noted from the above, two substrates are required for inducing the action of the present enzyme, one of the substrate being an epoxysuccinic acid and the other being a flavonoid or its analogous compound having at least one phenolic hydroxyl group. Besides the above-mentioned epoxysuccinic acids, the compounds having an epoxy ring, such as exo-3,4-epoxy-1,2,3,6-tetrahydrophthalic acid, can also used as a substrate of the present enzyme.

The activities of the present enzyme to the various substrate compounds having a phenolic hydroxyl group(s) shown in Table 1 in the presence of (±)-trans-epoxysuccinic acid were measured and shown as relative activities (%) with reference to the activity to genistein which was expressed as 100. An example of the result is shown in Table 1. The measurement of activity was conducted under the same conditions as used for the determination of titer described later.

TABLE 1

Substrate specificity in the presence of (±)-trans-epoxysuccinic acid

| Substrates | | Relative activity (%)* |
|---|---|---|
| genistein | (isoflavone) | 100 |
| daidzein | (isoflavone) | 52 |
| apigenin | (flavone) | 92 |
| kaempferol | (flavonol) | 278 |

TABLE 1-continued

Substrate specificity in the presence of (±)-trans-epoxysuccinic acid

| Substrates | | Relative activity (%)* |
|---|---|---|
| naringenin | (flavanone) | 194 |
| (+)-taxifolin | (dihydroflavonol) | 106 |
| sulfuretin | (aurone) | 316 |
| 4',6,7-trihydroxyisoflavone | (isoflavone) | 182 |
| biochanin A | (isoflavone) | 86 |
| baicalein | (flavone) | 321 |
| quercetin | (flavonol) | 31 |
| catechin | (catechin) | 16 |
| courmestrol | (rotenoid) | 58 |
| 5,7-dihydroxy-4-methylcoumarin | (coumarin) | 107 |
| 2',4',6',3,4-pentahydroxychalcone | (chalcone) | 115 |
| 6-hydroxy-2H-benzofuran-3-one | (coumaranone) | 135 |
| kojic acid | | 4 |
| coumaric acid | | 5 |
| vanillic acid | | 4 |

*Decrement of genistein as substrate was expressed as 100.

As is seen from Table 1, the enzyme of the present invention, in the presence of (±)-trans-epoxysuccinic acid, acts in a favorable way to the phenolic hydroxyl groups of the flavonoids having at least one phenolic hydroxyl group, e.g. isoflavones such as genistein, daidzein, 4',6,7-trihydroxyisoflavone and biochanin A, flavones such as apigenin and baicalein, flavanols such as kaempferol, flavanones such as naringenin, dihydroflavonols such as (+)-taxifolin, aurones such as sulfuretin, coumarins such as 5,7-dihydroxy-4-methylcoumarin and courmestrol, coumaranones such as 6-hydroxy-2H-benzofuran-3-one, chalcones such as 2',4',6',3,4-pentahydroxychalcone, coumorones, and rotenoids. The present enzyme acts faintly to the phenolic hydroxyl groups of kojic acid, coumarinic acid and vanillic acid.

Figure 2:
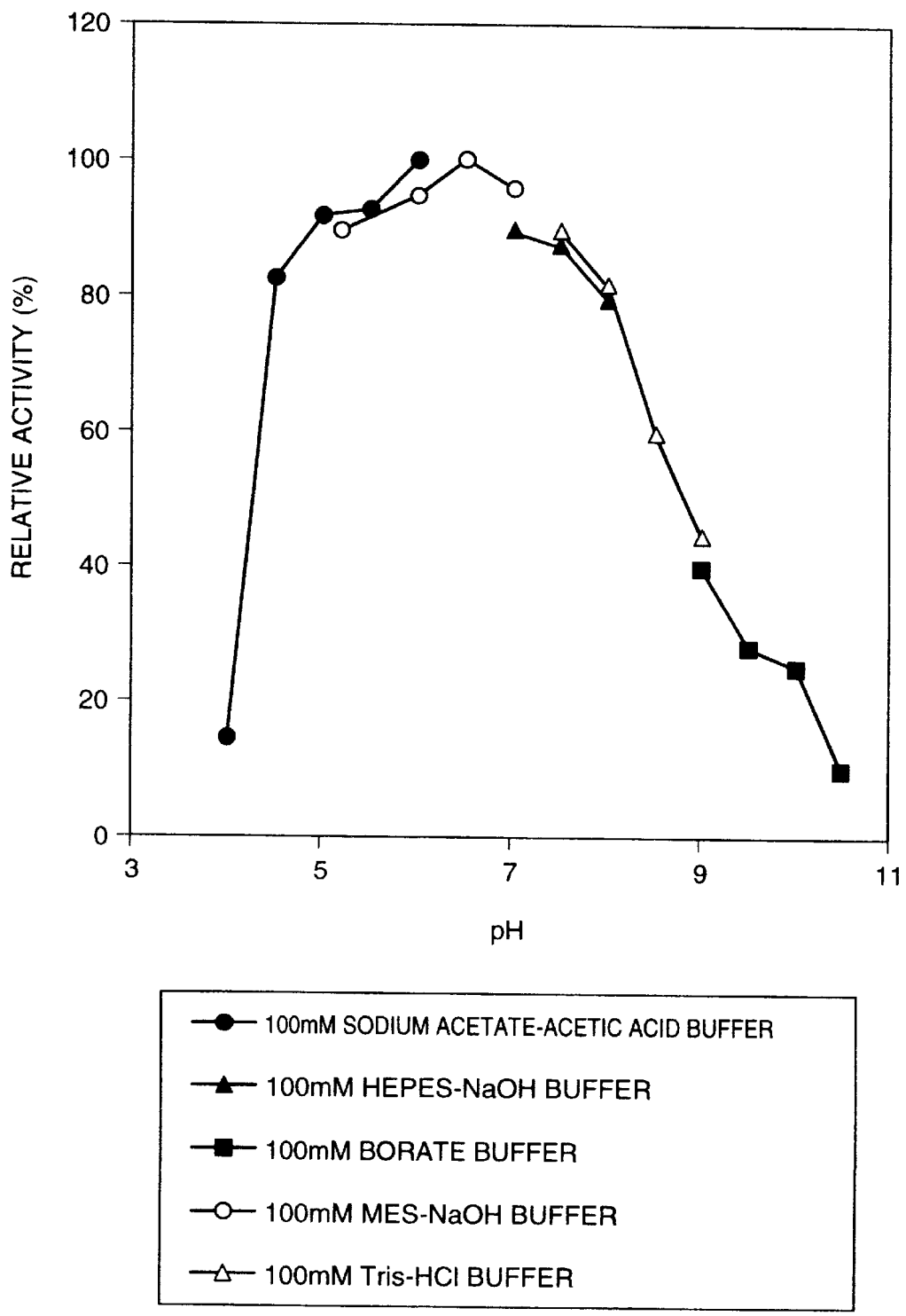
FIG. 2 is a graph showing the stable pH range of an enzyme according to the present invention.

(3) Optimal pH and Stable pH Range:

The optimal pH of the present enzyme was determined by measuring the activity of the enzyme at each pH in the defined range in the presence of (±)-trans-epoxysuccinic acid and genistein as substrates, using a 100 mM sodium acetate-acetic acid buffer (pH 4.0~6.0), a 100 mM MES-NaOH buffer (pH 5.2~7.0) and a 100 mM HEPES-NaOH buffer (pH 7.0~8.0). The result is shown in FIG. 1. It will be seen that the optimal pH of the present enzyme falls within the ambit of 4.8 to 5.5, particularly around 5.2. The stable pH range was determined by measuring the residual activity of the enzyme after treatment at 37° C. for 30 minutes using a 100 mM sodium acetate-acetic acid buffer (pH 4.0~6.0), a 100 mM MES-NaOH buffer (pH 5.2~7,0), a 100 mM HEPES-NaOH buffer (pH 7.0~8.0), a 100 mM Tris-hydrochloric acid buffer (pH 7.5~9.0) and a 100 mM borate buffer (pH 9.0~10.5). The result is shown in FIG. 2, from which it is noted that the stable pH range of the present enzyme is 4.5 to 8.0.

(4) Molecular Weight:

The molecular weight of the present enzyme was determined to be about 93,000 by SDS-polyacrylamide gel electrophoresis.

(5) Activation Factor:

A result of examination of the influence of various metallic ions on the action of the present enzyme is shown in Table 2. "Relative activity (%)" in Table 2 is the value relative to the activity (expressed as 100) observed when no metallic ion was added.

TABLE 2

Influence of metallic ions

| Metallic ions | Relative activity (%) |
|---|---|
| No addition | 100 |
| 5 mM EDTA | 12 |
| 20 mM $Mn^{2+}$ | 268 |
| 20 mM $Mg^{2+}$ | 220 |
| 20 mM $Zn^{2+}$ | 416 |
| 20 mM $Fe^{2+}$ | 125 |
| 20 mM $Fe^{3+}$ | 33 |
| 20 mM $Co^{2+}$ | 236 |
| 20 mM $Cu^{2+}$ | 0 |
| 20 mM $Ni^{2+}$ | 198 |
| 20 mM $Ca^{2+}$ | 140 |

The activity observed with no addition of metallic ions was expressed as 100%.
EDTA: ethylenediamine-N,N,N'N'-tetraacetic acid disodium salt As is seen from Table 2, the activity of the present enzyme is enhanced by the presence of such divalent metallic ions as $Zn^{2+}$, $Mn^{2+}$, $Co^{2+}$, $Mg^{2+}$, $Ni^{2+}$, $Ca^{2+}$ and $Fe^{2+}$, but is greatly inhibited in the presence of EDTA and $Cu^{2+}$.

(6) Determination of Titer:

Enzyme titer was determined by the following method. The amount of the enzyme that produces 1 μmol of 2-hydroxy-3-[[5-hydroxy-3-(4-hydroxyphenyl)-4-oxo-4H-1-benzopyran-7-yl]oxy]-butanedioic acid in one minute in the reaction of the following formula (6) is expressed as 1 U.

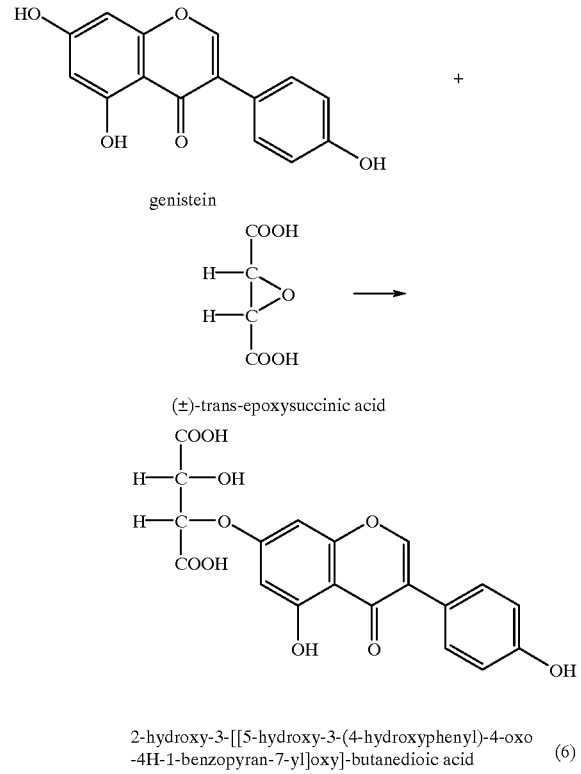

A. Preparation of Reagents:
<Substrate solutions>
Substrate solution I: 60 mM (±)-trans-epoxysuccinic acid (Tokyo Kasei Kogyo Co., Ltd.) was dissolved in 100 ml of a 50 mM sodium acetate-acetic acid buffer (pH 6.0), and the solution was adjusted to pH 6.0 with sodium hydroxide.

Substrate solution II: Prepared by dissolving 0.3 mmol of genistein (Funakoshi Co., Ltd.) in 100 ml of dimethyl sulfoxide.

<Buffer>

50 mmol of sodium acetate and 40 mmol of manganese sulfate were dissolved in distilled water, and the solution was adjusted to pH 6.0 with acetic acid and made one litre.

B. Reaction Conditions:

(1) 0.175 ml of the buffer, 0.1 ml of the substrate solution I and 0.01 ml of an enzyme solution were pipetted into a microtube, and the mixed solution was preincubated at 37° C. for 5 minutes.

(2) The above solution was mixed with 0.025 ml of the substrate solution II and reacted at 37° C. for 15 minutes, after which 0.01 ml of concentrated hydrochloric acid was added to stop the reaction. Used as control was a solution prepared in the same way as described above except that 0.01 ml of the buffer was added in place of 0.01 ml of the enzyme solution.

C. Determination of Reaction Product:

2-hydroxy-3-[[5-hydroxy-3-(4-hydroxyphenyl)-4-oxo-4H-1-benzopyran-7-yl]oxy]-butanedioic acid produced from the reaction of the formula (6) was determined by HPLC under the following conditions:

Column: Wakosil-II5C18HG (4.6 mm×30 mm+4.6 mm×250 mm, mfd. by Wako Pure Chemical Industries, Ltd.).

Eluent: distilled water containing 0.05% of trifluoroacetic acid and 28.8% of acetonitrile.

Flow rate: 1 ml/min.

Detecting wavelengh: 260 nm.

(9) Purification Method:

Conventional methods can be used for the isolation and purification of the present enzyme. For instance, one can use ammonium sulfate salting-out method, organic solvent precipitation method, adsorption method using ion exchanger, ion exchange chromatography, hydrophobic chromatography, gel filtration chromatography, adsorption chromatography, affinity chromatography, electrophoresis, etc. These techniques may be used either independently or in suitable combination.

(10) Km Value:

From the Lineweaver-Burk's plot, the Km value is 2.58× $10^{-3}$ M and 1.04×$10^{-3}$ M, respectively, when (±)-trans-epoxysuccinic acid and genistein are used as substrate.

(11) SDS-polyacrylamide Gel Electrophoresis:

Using a polyacrylamide gel having an acrylamide concentration gradient of 4–20% w/v, SDS polyacrylamide gel electrophoresis was carried out in the usual way. A single band was seen as shown in FIG. 3. Relative fluidity (Rf) after applying electric current for about 60 minutes was 0.38.

The process for producing the novel enzyme producing tartaric acid ether compound according to the present invention will now be explained. A typical example of the microorganisms capable of producing the present enzyme is the strains belonging to the genus Aspergillus, e.g. *Aspergillus oryzae* such as IFO 4206 and ATCC 20235, *Aspergillus sojae* such as ATCC 11906, ATCC 20245 and ATCC 20387, and *Aspergillus tamarii* such as IAM 13907 and IAM 2138. Varieties or variants of these strains are also usable. Of these strains, *Aspergillus oryzae* IFO 4206 is preferably used because of its particularly high potency to produce the present enzyme. The novel tartaric acid ether compound productive enzymes according to the present invention comprehend all of those enzymes which possess the principal ones of the above-defined physicochemical properties, such as the specified activities and substrate specificity, and the enzymes slightly different in other physicochemical properties are also included in the enzymes of the present invention. The above-mentioned microorganisms are but an exemplification of those usable for obtaining such tartaric acid ether compound productive enzymes. In the present invention, all of the microorganisms having an ability to produce a tartaric acid ether compound can be used.

For culture of the microorganisms having an ability to yield an enzyme producing tartaric acid ether compound, both liquid culture and solid culture can be employed, the latter being preferred. As for the medium for culturing such microorganisms, both synthetic and natural media can be used provided that they contain an appropriate carbon source, nitrogen source, inorganic matter and other necessary nutrients in proper amounts. A typical example of such media is a bran or the mixture of cooked soybean and roasted and crushed wheat. Culture of the microorganisms is conducted at 25 to 37° C., preferably around 30° C., for 30 to 150 hours, preferably 100 to 130 hours. By this operation, an enzyme of the present invention is generated and accumulated in the culture. The ordinary enzyme collecting means can be employed for collecting the produced enzyme from the culture.

Since the enzyme of the present invention essentially exists outside the organism, it is advisable to collect the present enzyme from the culture by means of extraction with water or a buffer solution. Then the culture is filtered or centrifuged to obtain a crude enzyme solution. For isolating the preferred enzyme from the crude enzyme solution, the above-mentioned purification methods can be employed. The enzyme obtained in the manner described above is of much avail for the production of tartaric acid ether compounds having one or more phenolic hydroxyl groups.

For producing a tartaric acid ether compound of this invention using the enzyme of the present invention, the use of the compounds capable of functioning as the two substrates is necessary. One of such substrates is an epoxysuccinic acid, particularly (±)-trans-epoxysuccinic acid being preferred in the present invention because of high reactivity. The other substrate is selected from the flavonoids having at least one phenolic hydroxyl group, for example, isoflavones (genistein, daidzein, 4',6,7-trihydroxyisoflavone, biochanin A, etc.), flavones (apigenin, baicalein, etc.), flavonols (kaempferol, quercetin, etc.), flavanones (naringenin, etc.), dihydroflavonols ((+)-taxifolin, etc.) and aurones (sulfuretin, etc.), or the flavonoid analogous compounds, for example, coumarins (5,7-dihydroxy-4-methylcoumarin, courmestrol, etc.), chalcones (2',4',6',3,4-pentahydrochalcone, etc.), coumaranones (6-hydroxy-2H-benzofuran-3-one, etc.), chromones and rotenoids. Of these flavonoids or their analogous compounds, genistein, 4',6,7-trihydroxyisoflavone, apigenin, baicalein, kaempferol, naringenin, (+)-taxifolin, sulfuretin, 5,7-dihydroxy-4-methylcoumarin, 2',4',6',3,4-pentahydroxychalcone, courmestrol and 6-hydroxy-2H-benzofuran-3-one are preferably used because of high reactivity.

The tartaric acid ether compounds provided according to the present invention are the compounds in which the phelonic hydroxyl group of a flavonoid or its analogous compound is bound to the epoxy ring of an epoxysuccinic acid to form ether linkage of one or more tartaric acid residues, and they can be produced by adding appropriate amounts of the purified or partially purified product of the enzyme of the present invention and a crude extract of the culture of a microorganism having an ability to produce the enzyme of the present invention to the said two substrates and reacting them. The tartaric acid ether compounds of the present invention can also be formed in a culture solution by adding a precursor substrate or substrates, such as the above-mentioned two substrates, to the medium used for culture of a microorganism having an ability to produce the enzyme of the present invention.

The reaction for producing a tartaric acid ether compound of the present invention is preferably carried out in a reaction solution using a buffer at a pH and a temperature in the ranges where the produced enzyme can stay stable, preferably a pH of 4.8 to 5.5 and a temperature of 30 to 55° C., for a period of 30 minutes to 80 hours, preferably 4 to 24 hours. As a consequence of the above operation, a tartaric acid ether compound of the present invention is formed in the reaction solution. The thus obtained tartaric acid ether compound having at least one phenolic hydroxyl group can be purified, for instance, by the following method.

The reaction solution containing a tartaric acid ether compound of the present invention is extracted with an organic solvent, such as ethyl acetate or n-propanol, either directly or after brought into an acidified state, and the concentrated solution is subjected to high-performance liquid chromatography (HPLC) using a reversed phase column. As the reversed phase column, there can be used the commercial products such as Wakosil-II5C18HG (Wako Pure Chemical Industries, Ltd.) and TSKgel ODS-120 T (Tosoh Corp.). The peak fraction newly produced from the enzyme reaction is separated to obtain the purified product of a tartaric acid ether compound.

Examples of the novel tartaric acid ether compounds provided according to the present invention include:

The tartaric acid ether compounds of sulfuretin represented by the following formula (7), produced by binding with ether linkage, the epoxy ring of an epoxysuccinic acid and the phenolic hydroxyl group at the 6-position of the A ring of sulfuretin:

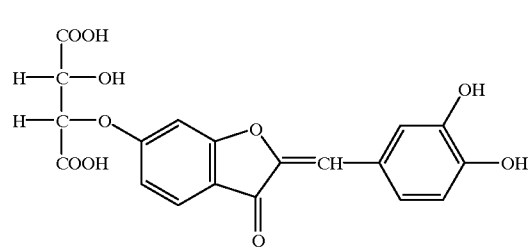

(7)

The tartaric acid ether compounds of kaempferol represented by the following formula (8), produced by binding with ether linkage, the epoxy ring of an epoxysuccinic acid and the phenolic hydroxyl group at the 7-position of the A ring of kaempferol or to the two phenolic hydroxyl groups at the 7-position of the A ring and at the 4'-position of the B ring:

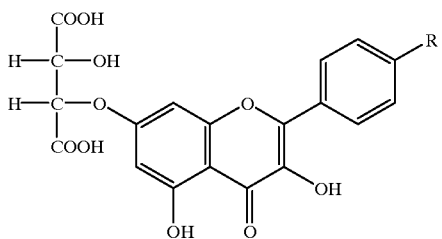

(8)

wherein R stands for —OH or —O—CH(COOH)—CH(OH)—COOH.

The tartaric acid ether compounds of naringenin represented by the following formula (9), produced by binding with ether linkage, the epoxy ring of an epoxysuccinic acid and the phenolic hydroxyl group at the 7-positon of the A ring of naringenin or to the two phenolic hydroxyl groups at the 7-position of the A ring and at the 4'-position of the B ring:

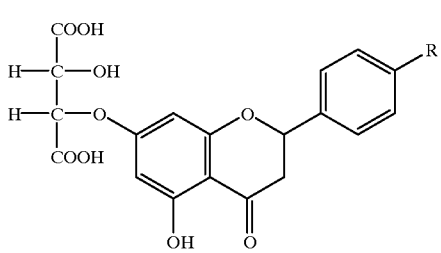

(9)

wherein R stands for —OH or —O—CH(COOH)—CH(OH)—COOH.

The tartaric acid ether compounds of (+)-taxifolin represented by the following formula (10), produced by binding with ether linkage, the epoxy ring of an epoxysuccinic acid and the phenolic hydroxyl group at the 7-position of the A ring of (+)-taxifolin:

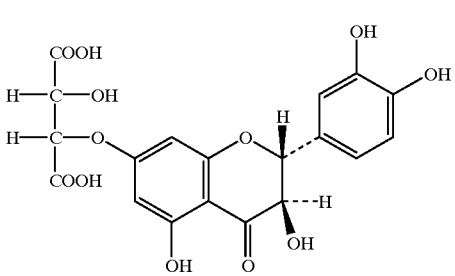

(10)

The tartaric acid ether compounds of apigenin represented by the following formula (11), produced by binding with ether linkage, the epoxy ring of an epoxysuccinic acid and the phenolic hydroxyl group at the 7-position of the A ring of apigenin:

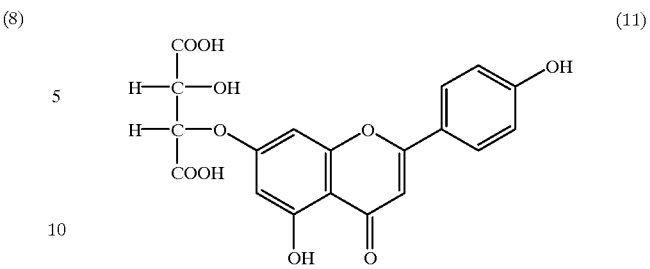

(11)

According to the process of the present invention, as described above, the preferred tartaric acid ether compounds of flavonoids or their analogous compounds can be easily and safely produced without requiring the complicate steps or specific expensive equipment for the synthesis, and the obtained tartaric acid ether compounds are expected to add to the innate actions of flavonoids or their analogous compounds, such as anti-ulcer action, anti-oxidant action and anti-decarboxylase inhibition activity. Also, because of their high water solubility and structural stability, these compounds are of avail as a base material of the pharmaceuticals, such as the perorally administered medicines, and functional foods.

PREFERRED EMBODIMENTS OF THE INVENTION

The present invention will be described in further detail with reference to the examples thereof, but the scope of the invention is not restricted to these examples.

EXAMPLE 1

(Preparation of an enzyme producing a tartaric acid ether compound)

In order to obtain a tartaric acid ether compound productive enzyme of the present invention, culture was carried out using Aspergillus oryzae in the following way. 30 g of wheat bran having a water content of 80% (w/v) was put into Ferunbach flasks and sterilized in an autoclave at 121° C. for 50 minutes, preparing 200 flasks of medium. Two platinum loops of Aspergillus oryzae (IFO4206) was inoculated into the medium in each tube from the stock slant and subjected to stationary culture at 30° C. for one week. Isolation and purification of the enzyme from the culture was conducted according to the following procedure.

Step 1 (Preparation of crude enzyme solution)

12 litres of a 50 mM sodium acetate-acetic acid buffer (pH 6.0) containing 0.1 mM phenylmethylsulfonyl fluoride) was added to the culture (5.05 kg), and the solution was extracted overnight at 5° C. and then subjected to gauze filtration and Celite filtration to obtain a crude extract solution.

Step 2 (Treatment with QAE-Sephadex A-50)

The crude extract (13 litres) obtained in Step 1 was added to 2 litres of QAE-Sephadex A-50 equilibrated with 50 mM sodium acetate-acetic acid buffer (pH 6.0) to obtain a non-adsorbed fraction (15 litres) having an enzyme activity and a 0.1 M NaCl eluted fraction (15 litres). The enzymatically active fractions were joined, concentrated by ultrafiltration, and dialyzed against 50 mM sodium acetate-acetic acid buffer (pH 6.0) containing 10 mM $MnSO_4$ and 10% glycerol (this buffer being hereinafter referred to as buffer A).

Step 3 (Treatment with ammonium sulfate)

Ammonium sulfate was added to the concentrated enzyme solution (1.4 litre) obtained in Step 2 to bring it to 80% saturation, and the mixed solution was stirred for 30 minutes and centrifuged at 5,000 rpm for 30 minutes to remove the supernatant. The precipitate was dissolved in 900 ml of the buffer A containing 1M ammonium sulfate and the solution was centrifuged at 5000 rpm for 30 minutes to remove the precipitate, thereby obtaining an enzyme solution. Step 4 (Phenyl-Sepharose CL-4B chromatography)

The enzyme solution (900 ml) obtained in Step 3 was adsorbed on a Phenyl-Sepharose CL-4B column (5 cm I.D.×20 cm), followed by washing of the column with the buffer A containing 0.8M ammonium sulfate, and eluted from the buffer A containing 0.8M ammonium sulfate (eluent I) by linear concentration gradient elution of the buffer A containing 30% ethylene glycol (eluent II). The active fraction eluted with the eluent II (approximately 80% conc) was collected, concentrated by ultrafiltration and dialyzed against the buffer A to obtain a concentrated enzyme solution.

Step 5 (Con A-Sepharose chromatography)

The concentrated enzyme solution (45 ml) obtained in Step 4 was adsorbed on a Con A-Sepharose column (2 cm I.D.×6.4 cm) equilibrated with the buffer A containing 0.5 M NaCl (pH 6.0), then the column was washed with the buffer A containing 0.5M NaCl and then with the buffer A containing 1.0M Nacl, and the product was eluted with the buffer A containing 1.0 M NaCl and 1.5 M α-methyl D-mannoside, the eluate being concentrated by ultrafiltration and dialyzed against a 20 mM sodium acetate-acetic acid buffer (pH 6.0) containing 10 mM $MnSO_4$ and 10% glycerol (this buffer being hereinafter referred to as buffer B).

Step 6 (MonoQ HR5/5 HPLC)

The concentrated enzyme solution (1 ml) obtained in Step 5 was adsorbed on a MonoQ HR5/5 ion exchange HPLC column (0.5 cm I.D.×5 cm), then the column was washed with the buffer B and the product was eluted with the buffer B containing 0~0.125 M NaCl by linear gradient elution. The active fraction eluted with about 0.1 M NaCl was collected and concentrated by ultrafiltration.

Step 7 (TSKgel G3000SW HPLC)

The enzyme solution (0.25 ml) obtained in Step 6 was passed through TSKgel G3000SW gel filtration HPLC columns (7.5 mm I.D.×60 cm×2) and subjected to gel filtration with the buffer A containing 0.1 M NaCl, and the eluted active fraction was collected, concentrated by ultrafiltration and dialyzed against the buffer A containing 1.8M ammonium sulfate.

Step 8 (TSKgel Ether-5PW HPLC)

The enzyme solution (0.1 ml) obtained in Step 7 was adsorbed on a TSKgel Ether-5PW hydrophobic HPLC column (7.5 mm I.D.×7.5 cm), followed by washing of the column with the buffer A containing 1.8M ammonium sulfate and elution by linear gradient elution with 1.8~0M ammonium sulfate. The active fraction eluted with about 1.2M ammonium sulfate was collected, concentrated by ultrafiltration and dialyzed against the buffer A to obtain a purified enzyme (0.135 ml). This fraction is a purified preparation of an enzyme of this invention, which has been determined to be homogeneous by SDS-polyacrylamide gel electrophoresis (FIG. 3). The total protein content of this preparation was 0.242 mg, its gross activity was 335 mU and its specific activity was 1,390 mU/mg.

EXAMPLE 2

(Preparation of a novel sulfuretin tartaric acid ether compound)

Solution (a): A solution prepared by dissolving 5 mg of commercial sulfuretin (Funakoshi Co., Ltd.) in 1 ml of dimethyl sulfoxide.

Solution (b): A solution prepared by dissolving 200 mM (±)-trans-epoxysuccinic acid (Tokyo Kasei Kogyo Co., Ltd.) in 2 ml of 100 mM sodium acetate-acetic acid buffer (pH 5.2) containing 20 mM $MnSO_4$ (as an activator) and 10% glycerol (as a stabilizer).

To a mixture of the above solutions (a) and (b) was added and mixed 0.012 ml of an enzyme of this invention obtained according to the procedure of Example 1, and the mixture was kept at 37° C. for 4 hours to let it undergo an enzyme reaction, after which 0.05 ml of concentrated hydrochloric acid was added to stop the reaction. The reaction solution was subjected to reversed phase HPLC (column: Wakosil-II5C18HG, 10 mm I.D.×300 mm, mfd. by Wako Pure Chemical Industries, Ltd.) adapted with a precolumn (column: Wakosil-II5C18HG, 10 mm I.D.×50 mm, Wako Pure Chemical Industries, Ltd.). The adsorbed fraction was eluted according to concentration gradient elution with acetonitrile containing 0.05% trifluoroacetic acid. The new peak fraction generated by the enzyme reaction was separated and evaporated to dryness by a rotary evaporator to obtain 5.7 mg of the enzyme reaction product.

The physicochemical properties of this enzyme reaction product were as follows. Appearance: yellow powder; Melting point: 224–228° C. (decomposed); Molecular weight: 402 ; Mass spectra (negative FAB-MS), m/z: 401 $(M-H)^-$, 269 $(sulfuretin-H)^-$; UV spectra: absorption at 258 and 398 nm (HPLC photodiode array analysis); IR spectra, KBr $(cm^{-1})$: 3450, 1650, 1620, 1510, 1460, 1400, 1250, 1210, 1140, 1100, 840, 760; $^1$H-NMR spectra, in DMSO-$d_6$, δ (ppm): 4.60 (1H, d, J=2.93 Hz, —CH—O—), 5.24 (1H, d, J=2.93 Hz, —CH—O), 6.68 (1H, s, =CH—), 6.75 (1H, d, J=2.22 Hz), 6.83 (1H, dd, J=2.14, 8.30), 6.99 (1H, d, J=2.14 Hz), 7.28 (1H, dd, J=2.14, 8.55 Hz), 7.44 (1H, d, J=2.14 Hz), 7.76 (1H,d, J=8.45 Hz), 9.26 (1H, br, OH); Solubility in solvents: soluble in water, methanol and DMSO.

The above instrumental analytical results led to the conclusion that the enzyme reaction product was a novel sulfuretin tartaric acid ether compound represented by the formula (7), produced by binding with ether linkage, the epoxy ring of an epoxysuccinic acid and the phenolic hydroxyl group at the 6-position in the A ring of sulfuretin.

EXAMPLE 3

(Preparation of a novel kaempferol tartaric acid ether compound)

The same procedure as used in Example 2 was conducted except that 7 mg of commercial kaempferol (Funakoshi Co., Ltd.) was used in lieu of 5 mg of sulfuretin in the solution (a). The reaction solution was passed through the HPLC column (same as used in Example 2) and the adsorbed fraction was collected. The new peak fractions I and II formed by the enzyme reaction were collected and evaporated to dryness by a rotary evaporator to obtain 1.4 mg of the enzyme reaction product I of the peak fraction I and 4 mg of the enzyme reaction product II of the peak fraction II.

(1) The physicochemical properties of the enzyme reaction product I were as follows: Appearance: yellow powder; Melting point: 247–250° C. (decomposed); Molecular weight: 418 ; Mass spectra (negative FAB-MS): m/z: 417 $(M-H)^-$, 285 $(kaempferol-H)^-$; UV spectra: absorption at 264 and 367 nm (HPLC photodiode array analysis); IR spectra, KBr $(cm^{-1})$: 3450, 1680, 1510, 1420, 1210, 1140, 1100, 840, 800, 730; $^1$H-NMR spectra, in DMSO-$d_6$, δ (ppm): 4.57 (1H, d, J=2.75 Hz, —CH—O—), 5.21 (1H, d, J=3.05 Hz, —CH—O—), 6.31 (1H, d, J=2.14 Hz), 6.74 (1H, d, J=2.14 Hz), 6.93 (2H, d, J=8.85 Hz), 8.10 (2H, d, J=8.85 Hz), 9.53 (1H, br, OH), 10.13 (1H, br, OH), 12.46 (1H, br, OH); Solubility in solvents: soluble in water, methanol and DMSO.

(2) The physicochemical properties of the enzyme reaction product II were as follows: Appearance: yellow powder; Melting point: 224–230° C.; Molecular weight: 550; Mass spectra (negative FAB-MS), m/z: 549 (M-H)$^-$, 417 (M-132-H)$^-$, 285 (kaempferol-H)$^-$; UV spectra: absorption at 264 and 367 nm (HPLC photodiode array analysis); IR spectra, KBr (cm$^{-1}$): 3450, 2930, 1650, 1560, 1540, 1510, 1460, 1420, 1360, 1320, 1240, 1170, 1130, 1100, 940, 890, 840; $^1$H-NMR spectra, in DMSO-d$_6$, δ (ppm): 4.56 (1H, d, J=3.05 Hz, —CH—O—), 4.58 (1H, d, J=2,75 Hz, —CH—O—), 5.14 (1H, d, J=3.05 Hz, —CH—O—), 5.22 (1H, d, J=3.05H, —CH—O—), 6.33 (1H, d, J=2.14 Hz), 6.76 (1H, d, J=2.14 Hz), 7.08 (2H, d, J=9.16 Hz), 8.18 (2H, d, J=9.16 Hz), 9.70 (1H, br, OH), 12.40 (1H, br, OH); Solubility in solvents: soluble in water, methanol and DMSO.

From the above results of instrumental analyses, the enzyme reaction product I of this Example was identified as a novel kaempferol tartaric acid ether compound represented by the formula (8) wherein R is —OH, in which the epoxy ring of an epoxysuccinic acid is combined with the phenolic hydroxyl group at the 7-position of the A ring of kaempferol, forming ether linkage of one tartaric acid residue. The enzyme reaction product II was identified as a novel kaempferol tartaric acid ether compound represented by the formula (8) wherein R is —O—CH(COOH)—CH(OH)—COOH, in which the epoxy ring of an epoxysuccinic acid is combined with the phenolic hydroxyl groups at the 7-position of the A ring of Kaempferol and at the 4'-position of the B ring to form ether linkage of two tartaric acid residues.

EXAMPLE 4

(Preparation of novel naringenin tartaric acid ether compound)

The same procedure as used in Example 2 was carried out except that 10 mg of commercial naringenin (Sigma Co., Ltd.) was used in place of 5 mg of sulfuretin in the solution (a). The reaction solution was passed through the HPLC column and the adsorbed fraction was collected. The new peak fractions I and II formed by the enzyme reaction were collected and evaporated to dryness by a rotary evaporator to obtain 6.7 mg of the enzyme reaction product of the peak fraction I and 1.2 mg of the enzyme reaction product of the peak fraction II.

(1) The physicochemical properties of the enzyme reaction product I were as follows. Appearance: pale yellow powder; Melting point: 209–216° C.; Molecular weight: 404; Mass spectra (negative FAB-MS), m/z: 403 (M-H)$^-$, 271 (naringenin-H)$^-$; UV spectra: absorption at 287 nm (HPLC photodiode array analysis); IR spectra, KBr (cm$^{-1}$): 3450, 2920, 1640, 1520, 1460, 1370, 1300, 1270, 1200, 1160, 1090, 890, 840; $^1$H-NMR spectra, in DMSO-d$_6$, δ (ppm): 2.73 (1H, m), 5 3.33 (1H, m), 4.51 (1H, m, —CH—O—), 5.12 (1H, m, —CH—O—), 5.50 (1H, m), 6.01 (1H, d, J=2.44 Hz), 6.02 (1H, d, J=2.44 Hz), 6.79 (2H, d, J=8.54 Hz), 7.33 (2H, d, J=8.55 Hz), 9.59 (1H, br, OH), 12.05 (1H, br, OH); Solubility in solvents: soluble in water, methanol and DMSO.

(2) The physicochemical properties of the enzyme reaction product II were as follows: Appearance: pale yellow powder; Melting point: 193–202° C. (decomposed); Molecular weight: 536; Mass spectra (negative FAB-MS): m/z: 535 (M-H)$^-$, 403 (M-132-H)$^-$, 271 (naringenin-H)$^-$; UV spectrum: absorption at 289 nm (HPLC photodiode array analysis); IR spectra, KBr (cm$^{-1}$): 3450, 2920, 1680, 1640, 1520, 1460, 1340, 1210, 1180, 1140, 1100, 840, 800, 720; $^1$H-NMR spectra, in DMSO-d$_6$, δ (ppm): 2.79 (1H, m), 3.32 (1H, m), 4.50 (2H, d, J=3.05 Hz, —CH—O—), 5.01 (1H, d, J=3.05 Hz, —CH—O—), 5.12 (1H, m, —CH—O—), 5.57 (1H, m), 6.02 (1H, m), 6.05 (1H, m), 6.95 (2H, d, J=8.85 Hz), 7.45 (2H, d, J=8.56 Hz), 12.04 (1H, s, OH); Solubility in solvents: soluble in water, methanol and DMSO.

The above results of instrumental analyses identified the enzyme reaction product I of this Example as a novel naringenin tartaric acid ether compound represented by the formula (9) wherein R is —OH, in which the epoxy ring of an epoxysuccinic acid is bound to the phenolic hydroxyl group at the 7-position of the A ring of naringenin to form ether linkage of one tartaric acid residue. The enzyme reaction product II was identified as a novel naringenin tartaric acid ether compound represented by the formula (9) wherein R is —O—CH(COOH)—CH(OH)—COOH, in which the epoxy ring of an epoxysuccinic acid is bound to the phenolic hydroxyl groups at the 7-position of the A ring of naringenin and at the 4'-position of the B ring to form ether linkage of 2 tartaric acid residues.

EXAMPLE 5

(Preparation of novel (+)-taxifolin tartaric acid ether compound)

The procedure of Example 2 was carried out using 12 mg of commercial (+)-taxifolin (Funakoshi Co., Ltd.) in place of 5 mg of sulfuretin in the solution (a). The reaction solution was passed through the HPLC column and the absorbed fraction was collected. The new peak fraction produced as a result of the enzyme reaction was collected and evaporated to dryness by a rotary evaporator to obtain 11 mg of the (+)-taxifolin enzyme reaction product.

The physicochemical properties of this enzyme reaction product were as described below. Appearance: white powder; Melting point: 155–163° C.; Molecular weight: 436; Mass spectra (negative FAB-MS), m/z: 435 (M-H)$^-$, 303 (taxifolin-H)$^-$; UV spectrum: absorption at 290 nm (HPLC photodiode array analysis); IR spectra, KBr (cm$^{-1}$): 3450, 2920, 1650, 1640, 1560, 1540, 1520, 1510, 1460, 1420, 1360, 1290, 1240, 1200, 1170, 1110, 1000, 950, 810, 770; $^1$H-NMR spectra, in DMSO-d$_6$, δ (ppm): 4.51 (1H, d, J=3.05 Hz, —CH—O—), 4.57 (1H, d, J=11.30 Hz), 5.04 (1H, d, J=11.30 Hz), 5.12 (1H, d, J=2.75 Hz, —CH—O—), 6.01 (1H, d, J=2.14 Hz), 6.05 (1H, d, J=2.14 Hz), 6.74 (1H, s), 6.75 (1H, s), 6.88 (1H, s), 11.80 (1H, br, OH); Solubility in solvents: soluble in water, methanol and DMSO.

From the above results of instrumental analyses, the enzyme reaction product was identified as a novel (+)-taxifolin tartaric acid ether compound represented by the formula (10), in which the epoxy ring of an epoxysuccinic acid is ether-linked to the phenolic hydroxyl group at the 7-position of the A ring of (+)-taxifolin.

EXAMPLE 6

(Preparation of novel apigenin tartaric acid ether compound)

The same procedure as used in Example 2 was carried out except that 5 mg of commercial apigenin (Funakoshi Co., Ltd.) was used in place of 5 mg of sulfuretin in the solution (a). The reaction solution was passed through the HPLC column and the adsorbed fraction was collected. The new peak fraction formed by the enzyme reaction was collected and evaporated to dryness by a rotary evaporator to obtain 1.4 mg of the apigenin enzyme reaction product.

The physicochemical properties of this enzyme reaction product were as follows: Appearance: pale yellow powder; Melting point: 268–274° C. (decomposed); Molecular weight: 402; Mass spectra (negative FAB-MS), m/z: 401 (M-H)$^-$, 269 (apigenin-H)$^-$; UV spectra: absorption at 267 and 337 nm (HPLC photodiode array analysis); IR spectra, KBr (cm$^{-1}$): 3450, 2930, 1650, 1640, 1620, 1560, 1500, 1460, 1240, 1210, 1180, 1120, 1090, 1030, 840, 770; $^1$H-NMR spectra, in DMSO-d$_6$, δ (ppm): 4.58 (1H, d, J=2.75 Hz, —CH—O—), 5.22 (1H, d, J=2.75 Hz, —CH—O—), 6.33 (1H, d, J=2.14 Hz), 6.78 (1H, d, J=2.14 Hz), 6.86 (1H, s), 6.93 (2H, d, J=8.85 Hz), 7.97 (2H, d, J=8.85 Hz), 10.39 (1H, br, OH), 12.94 (1H, br, OH); Solubility in solvents: soluble in water, methanol and DMSO.

From the above results of instrumental analyses, this enzyme reaction product was identified as a novel apigenin tartaric acid ether compound represented by the formula (11), in which the epoxy ring of an epoxysuccinic acid is ether-linked to the phenolic hydroxyl group at the 7-position of the A ring of apigenin.

The tartaric acid ether compound productive enzymes according to the present invention are the novel enzymes capable of producing the tartaric acid ether compounds by letting the phenolic hydroxyl groups of flavonoids or their analogous compounds act to the epoxy ring of an epoxysuccinic acid. Use of the present enzymes makes it possible to produce said tartaric acid ether compounds easily, precisely and safely at low cost according to the enzyme process, dispensing with the complicate operations and steps needed in the conventional chemical synthetic processes and without requiring any specific equipment for the synthesis. The tartaric acid ether compounds provided according to the present invention are expected to add to the innate activities of the flavonoids or their analogous compounds, such as anti-ulcer action, anti-oxidant action and dicarboxylase inhibitory action, and further, thanks to their high water solubility and structural stability, these compounds are of avail as a base material of pharmaceuticals, such as peroral medicines, and functional foods. Thus, the present invention is of great industrial utility.

What is claimed is:

1. An isolated enzyme preparation, said enzyme capable of catalyzing a reaction between an epoxy ring of an epoxysuccinic acid and a phenolic hydroxyl group of a flavonoid, or a flavonoid analogous compound to form a tartaric acid ether compound, wherein said enzyme has the following physiochemical properties:

(1) substrate specificity: the enzyme acts specifically to the substrate compounds, viz. epoxysuccinic acids and flavonoids or their analogous compounds having at least one phenolic hydroxyl group, and when the epoxysuccinic acid is (±)-trans-epoxysuccinic acid, the enzyme acts in a favorable way to the flavonoids having at least one phenolic hydroxyl group, including isoflavones, flavones, flavonols, flavanones, dihydroflavonols and aurones, and the flavonoid analogous compounds including coumarins, chalcones, coumaranones, chromones and rotenoids;

(2) optimal pH and stable pH range: when (±)-trans-epoxysuccinic acid and genistein are used as substrates, the optimal pH is 4.8 to 5.5 and the stable pH range is 4.5 to 8.0 for a treatment at 37° C. for a period of 30 minutes;

(3) molecular weight: the molecular weight as determined by SDS polyacrylamide gel electrophoresis is about 93,000.

2. The isolated enzyme preparation of claim 1 wherein said enzyme has been obtained from culturing a strain belonging to the genus Aspergillus.

3. An isolated enzyme preparation, said enzyme capable of catalyzing a reaction between an epoxy ring of an epoxysuccinic acid and a phenolic hydroxyl group of a flavonoid, or a flavonoid analogous compound to form a tartaric acid ether compound, wherein said enzyme has been obtained from culturing a strain belonging to the genus Aspergillus selected from the group consisting of *Aspergillus oryzae* IFO 4206, *Aspergillus oryzae* ATCC 20235, *Aspergillus sojae* ATCC 11906, *Aspergillus sojae* ATCC 20245, *Aspergillus sojae* 20387, *Aspergillus tamarii* IAM 13907, and *Aspergillus tamarii* IAM 2138.

4. An isolated enzyme preparation, said enzyme capable of catalyzing a reaction between an epoxy ring of an epoxysuccinic acid and a phenolic hydroxyl group of a flavonoid, or a flavonoid analogous compound to form a tartaric acid ether compound, wherein said enzyme has a molecular weight of about 93,000 as determined by SDS polyacrylamide gel electrophoresis, and wherein said enzyme has been obtained from culturing a strain belonging to the genus Aspergillus selected from the group consisting of *Aspergillus oryzae, Aspergillus sojae*, and *Aspergillus tamarii*.

* * * * *